US00PP12101P2

(12) United States Plant Patent
Sakazaki

(10) Patent No.: US PP12,101 P2
(45) Date of Patent: Sep. 25, 2001

(54) PETUNIA PLANT NAMED 'REVOLUTION BLUEVEIN NO.2'

(75) Inventor: Ushio Sakazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/263,210

(22) Filed: Mar. 5, 1999

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | | |
|---|---|---|---|---|
| P.P. 6,899 | | 7/1989 | Tsuda et al. | Plt./356 |
| P.P. 6,914 | | 7/1989 | Tsuda et al. | Plt./356 |
| P.P. 6,915 | | 7/1989 | Tsuda et al. | Plt./356 |
| P.P. 8,489 | | 12/1993 | Hirabayashi et al. | Plt./356 |
| P.P. 8,768 | | 6/1994 | Hirabayashi et al. | Plt./356 |
| P.P. 9,322 | | 10/1995 | Tachibana et al. | Plt./356 |
| P.P. 9,341 | | 10/1995 | Tachibana et al. | Plt./356 |
| P.P. 9,342 | | 10/1995 | Sakazaki et al. | Plt./356 |
| P.P. 9,556 | | 5/1996 | Tachibana et al. | Plt./356 |
| P.P. 9,557 | | 5/1996 | Suzuki et al. | Plt./356 |
| P.P. 9,754 | | 12/1996 | Suzuki et al. | Plt./356 |
| P.P. 10,045 | * | 9/1997 | Rother | Plt./356 |
| P.P. 10,278 | | 3/1998 | Murakami | Plt./356 |
| P.P. 10,279 | | 3/1998 | Murakami | Plt./356 |
| P.P. 10,287 | | 3/1998 | Murakami | Plt./356 |
| P.P. 10,310 | | 3/1998 | Sakazaki | Plt./356 |
| P.P. 10,330 | | 4/1998 | Sakazaki | Plt./356 |
| P.P. 10,355 | | 4/1998 | Murakami | Plt./356 |
| P.P. 11,006 | * | 7/1999 | Danziger | Plt./356 |

* cited by examiner

*Primary Examiner*—Bruce R. Campell
*Assistant Examiner*—Kent L. Bell
(74) *Attorney, Agent, or Firm*—Burns, Doane, Swecker & Mathis, L.L.P.

(57) ABSTRACT

Disclosed herein is a new and distinct variety of Petunia plant having a decumbent growth habit and long stems. The Petunia plant has abundant branching particularly with respect to primary branching, and great profusion of blooms with the entire plant remaining in bloom for a considerable period of time. The flowers are single and large with the petals having a pale purple ground color with a vivid purple vein pattern. The base color of the corolla throat is deep purple and the outside of the corolla tube is pale purple. The plant exhibits high resistance to rain, heat, drought and pests.

1 Drawing Sheet

BACKGROUND OF THE VARIETY

Figure 1:
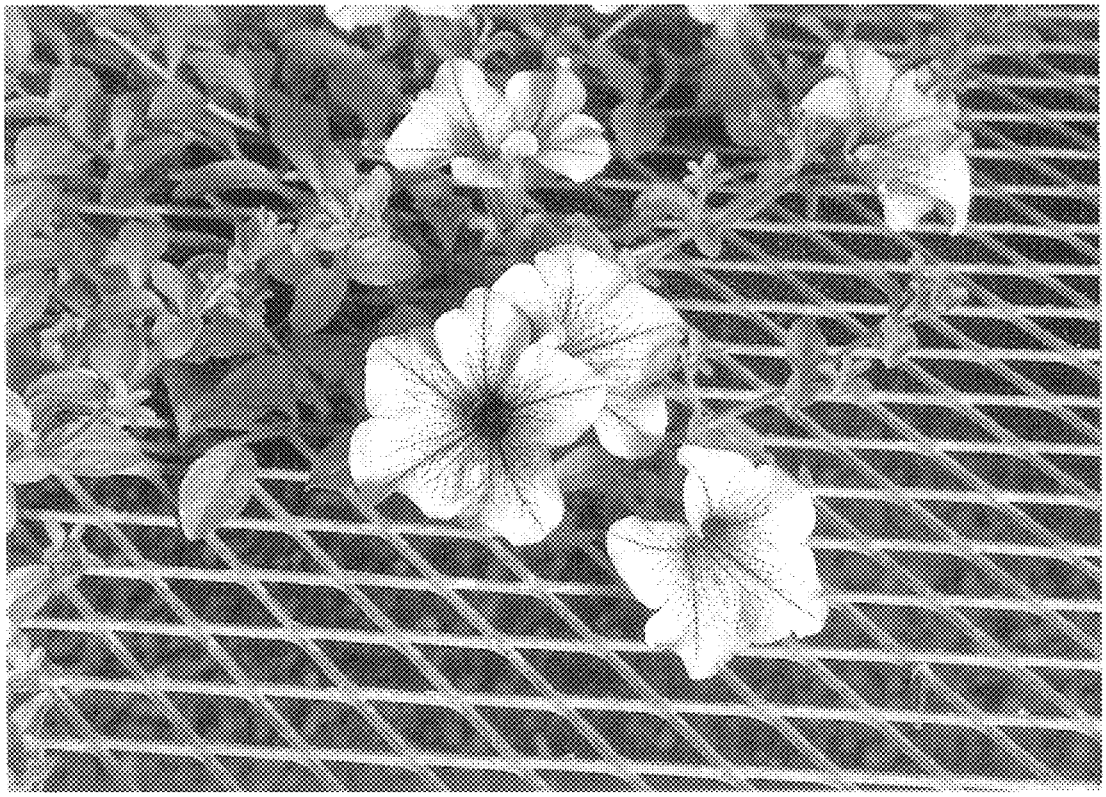

The Petunia is a very popular plant that is used for flower bedding and potting in the summer season. There are only a few Petunia varieties which do not have an upright growth habit and which have a high resistance to rain, heat, cold, and diseases. The Petunias of the Revolution series include 'Revolution Purplepink' (U.S. Plant Pat. No. 6,915), 'Revolution Brilliantpink' (U.S. Plant Pat. No. 6,914), 'Revolution Brilliantpink-mini' (U.S. Plant Pat. No. 6,899), and 'Revolution Bluevein' (U.S. Plant Pat. No. 9,322). These are decumbent type plants having long stems, a lower plant height, abundant branching, and a high resistance to heat, cold and rain. However, there are only a few Petunia varieties having a great profusion of flowers, pastel-colored flower petals and a high resistance to rain, heat, cold and diseases. Accordingly, this invention was aimed at obtaining a new Petunia variety having pale purple colored petals with a vivid purple vein pattern, together with the above features.

The new variety of *Petunia×hybrida* Hort. plant according to this invention originated from crossing the 'Blue Daddy' (♀) variety (non-patented in the United States) and a wild type of Petunia plant 'NW-1' (♂) native to Brazil (non-patented in the United States).

Initially, 75 seedlings were obtained from crossing the 'Blue Daddy' variety as female parent and the 'NW-1' wild type of Petunia plant as pollen parent in July 1994. From this crossing 4 seedlings were selected in view of their decumbent growth habit and pale purple colored petals with a vivid purple vein pattern. These 4 seedlings were grown and were tested during potting and bedding trials. Only one plant of the present invention was selected in 1995. The botanical characteristics of the finally-selected plant were then examined, using similar variety 'Revolution Bluevein' (U.S. Plant Pat. No. 9,322) for comparison. As a result, it was concluded that this new Petunia is distinguishable from any other variety, whose existence is known to us, and is uniform and stable in its characteristics following asexual propagation by the use of cuttings at Mishima gun, Oosaka-fu, Japan. The new variety of Petunia of the present invention was named 'Revolution Bluevein No.2'.

In the following description, the color information is in accordance with The R.H.S. Colour Chart of The Royal Horticultural Society, London, England. A color chart based on The Japan Color Standard for Horticultural Plants (J.H.S. Color Chart) is also added for reference.

The new variety of the present invention can be readily distinguished from its 'Blue Daddy' female parent. More specifically, the growth habit of the 'Blue Daddy' variety is erect and spreading while that of the new variety is decumbent and spreading. Also, the primary and secondary branching of the new variety is more abundant.

The seeds of the 'NW-1' male parent of the new variety of the present invention were gathered at Gramado, Rio Grande Do Sul, Brazil, and were introduced to Japan in October, 1983. The main botanical characteristics of the 'NW-1' male parent used in the breeding of the new 'Revolution Bluevein No. 2' variety are as follows:

Plant:
*Growth habit.*—Decumbent.
*Plant height.*—20 cm.
*Spreading area of plant.*—100–150 cm in diameter.
*Blooming period.*—May to August in the southern Kanto area, Japan.
Stem:
*Length.*—50–80 cm.
*Thickness.*—Main stem 2.0–3.0 mm; and lateral stem 1.5–2.5 mm.
*Pubescence.*—Dense.
*Branching.*—Very abundant.
*Length of internode.*—1.0–2.0 cm before blooming; and 1.5–3.0 cm during blooming.
*Color.*—Strong yellow green (R.H.S. 144B–144C, J.H.S. 3512–3513).
Leaf:
*Shape.*—Oval.
*Length.*—4.5–5.5 cm.
*Width.*—2.5–3.5 cm.
*Color.*—Grayish olive green (R.H.S. 137A–137B, J.H.S. 3716–3717).
*Phyllotaxis.*—Opposite both before and during blooming.
*Pubescence.*—Sparse.
Flower:
*Facing direction.*—Opening obliquely upward.
*Type.*—Single.
*Shape.*—Funnel-shape, with five petals.
*Diameter.*—4.0–5.0 cm.
*Color.*—In the unopened stage (bud), dark reddish purple (R.H.S. 79B, J.H.S. 8907–8909); when open, vivid reddish purple (R.H.S. 74A, J.H.S. 9207), and at full bloom, vivid reddish purple (R.H.S. 80A, J.H.S. 8906).
*Reproductive organs.*—1 pistil and 5 stamens.
*Peduncle.*—0.9–1.2 mm in thickness, and 2.0–2.5 cm in length.
*Physiological and ecological characteristics.*—High resistance to cold, relatively high resistance to heat, and moderate resistance to disease and pests.

The botanical characteristics of 'Revolution Bluevein', which is similar variety to the new Petunia plant 'Revolution Bluevein No. 2', are as follows:

Plant:
*Growth habit.*—Decumbent. The stems hang down when potted in a hanging pot.
*Plant height.*—20–25 cm.
*Spreading area of plant.*—The stems extend to length of 70–80 cm from the base, and thus the spreading area of the plant is 140–160 cm in diameter.
*Growth.*—Very vigorous with abundant branching, and a great profusion of blooms with the entire plant remaining in bloom for a considerable period of time.
*Blooming period.*—Late March to the beginning of October in the southern Kanto area of Japan. The plant shape does not change throughout this period.
Stem:
*Thickness.*—Medium; 4.0–6.0 mm.
*Pubescence.*—Present.
*Branching.*—Abundant. Especially the primary branching is very abundant.
*Length of internode.*—Short; 2.0–4.0 cm.
*Anthocyanin pigmentation*—Absent.
Leaf:
*Shape.*—Lanceolate.
*Length.*—3.0–4.0 cm.
*Width.*—1.5–3.5 cm.
*Color.*—Moderate yellow green (R.H.S. 137C, J.H.S. 3712).
*Attaching angle.*—Horizontal.
*Thickness.*—Medium; 0.6–0.8 cm.
*Pubescence.*—Present.
Flower:
*Facing direction.*—Slanting upward.
*Type.*—Single.
*Shape.*—Funnel-shaped, with five petals.
*Waving of petal.*—Weak.
*Lobation of petal.*—Shallow.
*Petal shape at tip.*—Obverse.
*Petal color fading.*—Medium.
*Diameter.*—Small; 5.0–6.0 cm.
*Petal bi-color.*—Present.
*Petal variegated pattern of corolla.*—Vein pattern.
*Petal ground color.*—Very pale purple (R.H.S. 91C–91D, J.H.S. 8301–8302).
*Petal color of variegated pattern.*—Moderate purple (R.H.S. 83A, J.H.S. 8608). Bottom color of the corolla throat is vivid purple (R.H.S. 88A, J.H.S. 8306). The outside of corolla tube is very pale purple (R.H.S. 91D, J.H.S. 8302).
*Reproductive organs.*—1 pistil and 5 stamens.
*Physiological and ecological characteristics.*—High resistance to rain, heat, drought and-moderate resistance to pests.

SUMMARY OF THE VARIETY

The new variety of the present invention has a decumbent growth habit, very abundant branching and forms great profusion blooms with the whole plant remaining in bloom for a considerable period of time. The flowers are single and large. The petals have a pale purple coloration with vivid deeper purple vein pattern, and medium petal waving. The plant has a high resistance to rain, heat, cold, drought and pests.

BRIEF DESCRIPTION OF THE PHOTOGRAPH

FIG. 1 is a photograph of flowers and leaves of the new variety of Petunia plant 'Revolution Bluevein No.2'.

DESCRIPTION OF THE NEW VARIETY

The botanical characteristics of the new and distinct variety of Petunia plant named 'Revolution Bluevein No.2' are as follows when observing during December at Mishima-gun, Oosaka-fu, Japan young plants that had been reproduced by cuttings during the preceding June:

Plant:
*Growth habit.*—Decumbent. The stems hang down when potted in a hanging pot.
*Plant height.*—10–15 cm.
*Spreading area of plant.*—The stem extends to length of 60–75 cm from the base, and thus the spreading area of the plant is 130–150 cm in diameter.
*Growth.*—Very vigorous with abundant branching, and a great profusion of blooms with the whole plant remaining in bloom for a considerable period of time. It takes approximately 12 weeks to produce a flowering plant from a cutting.

*Blooming period.*—Late March to late September in the southern Kanto area, Japan. The plant shape does not change throughout this period. A typical flower commonly lasts approximately 5 days on the plant when experiencing a temperature of approximately 20° C.

Stem:

*Thickness.*—Medium and commonly approximately 2.4 mm.

*Pubescence.*—Present.

*Branching.*—Very abundant.

*Length of internode.*—Long and commonly approximately 16 mm.

*Anthocyanin pigmentation.*—Present and near R.H.S. 152A.

Leaf:

*Shape.*—Elliptic with an obtuse base, acute apex, and an entire margin.

*Length.*—2.5–4.0 cm.

*Width.*—1.5–2.0 cm.

*Color.*—Dark yellow green to strong yellow green (R.H.S. 145A–146A, J.H.S. 3508–3512) on the upper surface and strong yellow green (R.H.S. 144A) on the under surface.

*Attaching angle.*—Horizontal and sessile without petioles.

*Thickness.*—Medium approximately 0.2 mm.

*Pubescence.*—Present.

Bud:

*Shape.*—Elongated and tubular.

*Length.*—Approximately 43 mm just prior to opening.

*Diameter.*—Approximately 7.3 mm just prior to opening.

*Color.*—Moderate reddish-purple, R.H.S. 79C.

Flower:

*Facing direction.*—Horizontal.

*Type.*—Single.

*Shape.*—Funnel-shape, with five deeply-lobed petals.

*Shape of corolla tube.*—Tubular and expanding toward the open end.

*Waving of petal.*—Medium.

*Lobation of petal.*—Shallow.

*Petal apex.*—Rounded.

*Petal color fading.*—Weak.

*Diameter.*—7.5–9.0 cm.

*Depth.*—Approximately 44 mm during the course of opening.

*Petal bi-color.*—Present.

*Petal variegated pattern of corolla.*—Vein pattern.

*Petal ground color (both surfaces).*—Pale purple (R.H.S. 69B–73D, J.H.S. 8602).

*Petal color of variegated pattern (both surfaces).*—Vivid purple (R.H.S. 81B–82B, J.H.S. 8605). Bottom color of the corolla throat is deep purple (R.H.S. 86A, J.H.S. 8608). The outside of corolla tube is pale purple (R.H.S. 69B–73D, J.H.S. 8602).

*Sepal.*—There is one obtusely lobed sepal that surrounds the base of the corolla. The coloration is light yellow green (R.H.S. 144D) with some moderate reddish purple (R.H.S. 79C) (both surfaces).

*Peduncle.*—Olive-gray in coloration (R.H.S. 152B), firm, approximately 23 mm in length and approximately 1.5 mm in diameter.

*Reproductive organs.*—1 pistil and 5 stamens.

*Anthers.*—Pale yellow green in coloration (R.H.S. 4D), and the length commonly is approximately 1.7 mm.

*Filaments.*—White in coloration (R.H.S. 155A) and the length commonly is approximately 16 mm.

*Stigma.*—Moderate yellow-green in coloration (R.H.S. 137D).

*Style.*—Pale yellow-green (R.H.S. 145D) in coloration and the length commonly is approximately 13 mm.

*Ovary.*—Light yellow-green (R.H.S. 149C) in coloration, the length is approximately 2 mm and the diameter is approximately 1.2 mm.

*Pollen.*—Formed in sparse quantity and white in coloration (R.H.S. 155C).

*Seeds.*—Rarely formed.

*Fragrance.*—None.

*Physiological and ecological characteristics.*—High resistance to rain, heat, drought and pests. High resistance to aphids, thrips, powdery mildew and Botrytis is exhibited.

This new variety of Petunia plant is most suitable for flower bedding and potting, particularly in hanging pots or planters, and is excellent for use as ground cover. Pinching of old blossoms will enhance the formation of new blossoms.

I claim:

1. A new and distinct variety of Petunia plant, substantially as herein illustrated and described, characterized particularly as to novelty by (A) a decumbent growth habit with long stems, (B) abundant branching and great profusion of blooms with the entire plant remaining in bloom for a considerable period of time, (C) flowers are single and large, the petals have a pale purple ground color with a vivid purple vein pattern, and the base color of the corolla throat is deep purple and the outside of corolla tube is pale purple, and (D) a high resistance to rain, heat, drought and pests.

* * * * *